US012637702B2

(12) United States Patent
Cinqualbre et al.

(10) Patent No.: US 12,637,702 B2
(45) Date of Patent: May 26, 2026

(54) PROCESS FOR PREPARING SUBSTITUTED IMIDAZO[1,5-α]PYRAZINES

(71) Applicant: Hoffmann-La Roche Inc., Little Falls, NJ (US)

(72) Inventors: Joséphine Eliette Françoise Cinqualbre, Saint-Louis (FR); Stefan Hildbrand, Gelterkinden (CH); Paolo Tosatti, Binningen (CH); Kurt Puentener, Ueken (CH); Dennis Wetzl, Riehen (CH); Hans Iding, Magden (CH); Patrick Stocker, Basel (CH); Nicolas Mickael Fédou, Huningue (FR); Paul Spurr, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 716 days.

(21) Appl. No.: 17/997,337

(22) PCT Filed: Apr. 26, 2021

(86) PCT No.: PCT/EP2021/060771
§ 371 (c)(1),
(2) Date: Oct. 27, 2022

(87) PCT Pub. No.: WO2021/219523
PCT Pub. Date: Nov. 4, 2021

(65) Prior Publication Data
US 2023/0175026 A1 Jun. 8, 2023

(30) Foreign Application Priority Data
Apr. 28, 2020 (EP) .................................... 20171689

(51) Int. Cl.
*C07D 487/04* (2006.01)
*C07D 241/04* (2006.01)
*C12P 17/12* (2006.01)

(52) U.S. Cl.
CPC ............ *C12P 17/12* (2013.01); *C07D 241/04* (2013.01); *C07D 487/04* (2013.01)

(58) Field of Classification Search
CPC .................................................... C07D 487/04
(Continued)

(56) References Cited

U.S. PATENT DOCUMENTS 6,214,604 B1 4/2001 Kiener et al.

FOREIGN PATENT DOCUMENTS

CN 101648915 A 2/2010
WO 2015/132276 9/2015
WO 2017/140750 8/2017

OTHER PUBLICATIONS

International Search Report—PCT/EP2021/060771, (w/Written Opinion),:pp. 1-13 (Jun. 17, 2021).
(Continued)

*Primary Examiner* — Douglas M Willis
(74) *Attorney, Agent, or Firm* — Genentech, Inc.

(57) ABSTRACT

Disclosed herein are processes for the preparation of fused heteroaryl dihydro pyrimidine compounds, or salts or stereoisomers thereof, which are useful for the treatment and prophylaxis of hepatitis B virus infections using compounds of formula IX or stereoisomers thereof,

IX

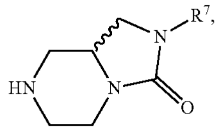

wherein a disclosed process comprises
a. reacting a compound formula II

II

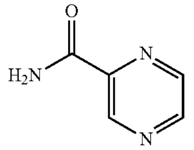

with hydrogen in the presence of a solvent and a palladium catalyst or a platinum catalyst, to form a compound of formula III:

III

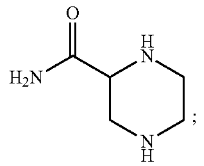

b. reacting the compound of formula III, or a salt or stereoisomer thereof, with a hydrolase selected from the group consisting of an amidase and a peptidase, or a mixture thereof, to form a compound of formula I:

I

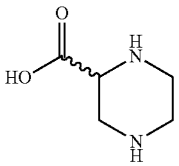

(Continued)

or a salt or stereoisomer thereof, c. protecting the compound of formula I, or a salt or stereoisomer thereof, with an amino protecting group (PG) selected from the group consisting of di-tert-butyl dicarbonate ($Boc_2O$) and 2-(tert-butoxycarbonyloxyimino)-2-phenylacetonitrile, to form a compound of formula IV:

IV

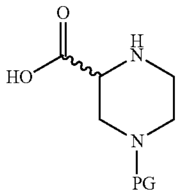

d. reacting the compound of formula IV, or a salt or stereoisomer thereof, with a compound of the following formula: —$R^7$—$NH_2$ in the presence of a base and the coupling agent, carbonyldiimidazole (CDI), to form a compound of formula V:

V

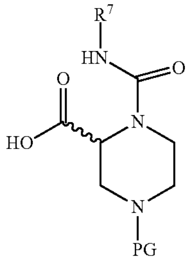

or a salt or stereoisomer thereof, e. reacting the compound of formula V above, or a salt or stereoisomer thereof, with oxalyl chloride to form a compound of formula VI

VI

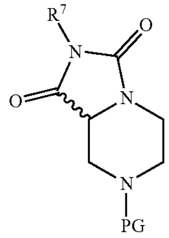

f. reacting the compound of formula VI above, or a stereoisomer thereof, with a reducing agent selected from the group consisting of $BH_3 \cdot THF$ and $NaBH_4$, to form a compound of formula VII:

VII

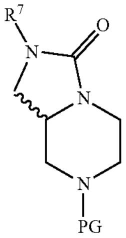

; and g. deprotecting the compound of formula VII above, or a stereoisomer thereof, with concentrated HCl in methyl isobutyl ketone (MIBK), to form a compound of formula IX:

IX

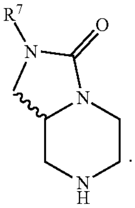

.

7 Claims, No Drawings

Specification includes a Sequence Listing.

(58) Field of Classification Search
USPC .......................................................... 544/350
See application file for complete search history.

(56) References Cited

OTHER PUBLICATIONS

International Preliminary Report on Patentability—PCT/EP2021/060771,:pp. 1-6 (Oct. 27, 2022).
Eichhorn, E., et al., "Preparation of (S)-piperazine-2-carboxylic acid, (R)-piperazine-2-carboxylic acid, and (S)-piperidine-2-carboxylic acid by kinetic resolution of the corresponding racemic carboxamides with stereoselective amidases in whole bacterial cells" Tetrahedron: Asymmetry 8(15):2533-2536 (Aug. 14, 1997).
Bruce et al., "Kinetic Resolution of Piperazine-2-Carboxamide by Leucine Aminopeptidase. An Application in the Synthesis of the Nucleoside Transport Blocker (-) Draflazine" Synthetic Communications 25(17):2673-2684 ( 1995).
Komeda et al., "S-Stereoselective piperazine-2-tert-butylcarboxamide hydrolase from Pseudomonas azotoformans IAM 1603 is a novel L-amino acid amidase" Eur J. Biochem 271:1465-1475 (Feb. 2004).
Zhi-Tang et al., "Screening and identification of bacterical strains capable of producing single enantiomers of piperazine-2-carboxylic acid" Journal of Agricultural University of Hebei (w/Eng Abstract) 35(3):69-74 (May 2012).

PROCESS FOR PREPARING SUBSTITUTED IMIDAZO[1,5-α]PYRAZINES

CROSS-REFERENCE TO RELATED APPLICATIONS

This application is the National Stage Entry under 35 U.S.C. § 371 of International Application No. PCT/EP2021/060771, filed Apr. 26, 2021, which claims benefit of priority under 35 U.S.C. § 119 (a) to EP Application Serial No. 20171689.1 filed on Apr. 28, 2020, each of which is incorporated herein by reference in its entirety.

DETAILED DESCRIPTION

The invention relates to a novel process for the preparation of a chiral piperazine-2-carboxylic acid of the formula I

I

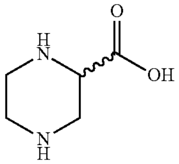

The chiral piperazine-2-carboxylic acid derivatives of the formula I are key intermediates for the preparation of fused heteroaryl dihydro pyrimidines which are useful for the treatment and prophylaxis of hepatitis B virus infections (PCT Publications WO 2015/132276).

A process for the preparation of chiral piperazine-2-carboxylic acid has been described by Eichhorn et al. *Tetrahedron Asymmetry*, Vol. 8, No. 15, pp. 2533-2536, 1997. Racemic piperazine-2-carboxamide has been kinetically resolved with bacterial cells from *Klebsiella terrigena* and *Burkholderia* sp. However, for technical scale synthesis, it would be desirable to use isolated and characterized enzymes to run the process on higher enzyme and substrate concentrations. The object of the present invention therefore was to create a process, which can be performed on technical scale.

The object could be reached with the process as outlined below, which comprises the steps a) the catalytic hydrogenation of pyrazine-2-carboxamide of the formula II

II

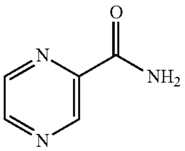

to form the piperazine-2-carboxamide of formula III

III

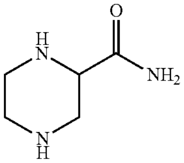

and b) the enzymatic conversion of the piperazine-2-carboxamide of formula III with a hydrolase to form the chiral piperazine-2-carboxylic acid or a salt thereof of the formula I The following definitions are set forth to illustrate and define the meaning and scope of the various terms used to describe the invention herein.

The term "amino protecting group" refers to an acid or Lewis acid sensitive substituent conventionally used to hinder the reactivity of the amino group. Suitable acid or Lewis acid sensitive amino protecting groups are described in Green T., "Protective Groups in Organic Synthesis", 4th Ed. by Wiley Interscience, 2007, Chapter 7, 696 ff. Suitable amino protecting groups for PG can therefore be selected from Boc (tert-butoxycarbonyl), benzyl, 4-methoxybenzyl, benzhydryl, Fmoc (fluorenylmethoxycarbonyl), Cbz (benzyloxycarbonyl), Moz (p-methoxybenzyl carbonyl), Troc (2,2,2-trichloroethoxycarbonyl), Teoc (2-(Trimethylsilyl) ethoxycarbonyl), Adoc (adamantoxycarbonyl), formyl, acetyl or from cyclobutoxycarbonyl. Preferred amino protecting group is Boc.

The spiral bond

""

stands for "" or for "" thus indicating chirality of the molecule.

Whenever a chiral carbon is present in a chemical structure, it is intended that all stereoisomers associated with that chiral carbon are encompassed by the structure as pure stereoisomers as well as mixtures thereof.

Step a)

Step a) requires the catalytic hydrogenation of pyrazine-2-carboxamide of the formula II

II

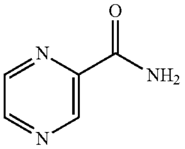

to form the piperazine-2-carboxamide of formula III

III

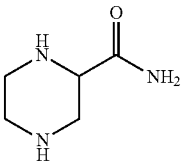

Pyrazine-2-carboxamide is a widely commercially available compound.

The catalytic hydrogenation is typically performed with hydrogen in the presence of a metal hydrogenation catalyst and a solvent.

Suitable metal in the metal hydrogenation catalyst is Palladium or Platinum, preferably Palladium.

The metal is as a rule applied on an inert support selected from carbon or aluminum oxide, preferably on carbon. Usual metal loading (w/w) on support are 0.5% to 20%, preferably 3% to 15%, more preferably 8 to 12%. Most preferred metal hydrogenation catalyst is 10% Palladium on carbon (10% Pd/C).

The metal hydrogenation catalyst is usually used in an amount of 3% to 20% w/w, typically in an amount of 10% w/w related to the pyrazine-2-carboxamide starting material.

The solvent can be an organic solvent selected from an aliphatic alcohol such as methanol or ethanol or from water or from mixtures thereof. Preferred solvent is water.

The catalytic hydrogenation is expediently performed at a reaction temperature of 20° C., to the boiling temperature of the respective solvent, preferably from 30° C., to 60° C., more preferably from 35° C., to 45° C., at a hydrogen pressure from 5 bar to 50 bar, preferably from 15 bar to 25 bar.

In the most preferred embodiment, the catalytic hydrogenation is performed with a 10% Pd/C 10% w/w catalyst in water at a reaction temperature of 40° C., and a hydrogen pressure of 20 bar.

The resulting piperazine-2-carboxamide can be isolated by procedures known for the skilled in the art such as by a separation of the catalyst from the reaction mixture and by the subsequent removal of the solvent from the filtrate.

However, in a preferred embodiment, the piperazine-2-carboxamide is not isolated and after separation of the catalyst from the reaction mixture further processed in step b).

Still in a further preferred embodiment the catalyst, after separating it from the reaction mixture, can be re-used several times, typically at least 5 times, without significant decrease of performance. If applicable, a decrease in catalyst performance can be compensated by adding fresh catalyst.

Step b)

Step b) requires the enzymatic conversion of the piperazine-2-carboxamide of formula III with a hydrolase to form the chiral piperazine-2-carboxylic acid of formula I.

Hydrolases suitable for the enzymatic conversion are typically peptidases, amidases, or mixtures thereof.

In a preferred embodiment hydrolases are selected which have the potential to form the (S)-piperazine-2-carboxylic acid of the formula Ia Ia

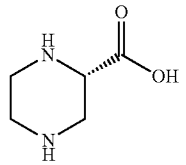

with an enantiomeric excess of at least 90%, preferably at least 95% more preferably at least 98%.

A representative of a preferable hydrolase that is capable to form the (S)-piperazine-2-carboxylic acid of the formula Ia has an amino acid sequence that is at least 80%, at least 85%, at least 90% or at least 95% identity to the amino acid sequence of SEQ ID NO 1.

```
                                                                   SEQ ID NO 1
MRSLLWASLL SGVLAGRALV SPDEFPEDIQ LEDLLEGSQQ LEDFAYAYPE RNRVFGGKAH   60

DDTVNYLYEE LKKTGYYDVY KQPQVHLWSN ADQTLKVGDE EIEAKTMTYS PSVEVTADVA  120

VVKNLGCSEA DYPSDVEGKV ALIKRGECPF GDKSVLAAKA KAAASIVYNN VAGSMAGTLG  180

AAQSDKGPYS AIVGISLEDG QKLIKLAEAG SVSVDLWVDS KQENRTTYNV VAQTKGGDPN  240

NVVALGGHTD SVEAGPGIND DGSGIISNLV IAKALTQYSV KNAVRFLFWT AEEFGLLGSN  300

YYVSHLNATE LNKIRLYLNF DMIASPNYAL MIYDGDGSAF NQSGPAGSAQ IEKLFEDYYD  360

SIDLPHIPTQ FDGRSDYEAF ILNGIPSGGL FTGAEGIMSE ENASRWGGQA GVAYDANYHA  420

AGDNMTNLNH EAFLINSKAT AFAVATYAND LSSIPKRNTT SSLHRRARTM RPFGKRAPKT  480

HAHVSGSGCW HSQVEA.                                                 496
```

Some enzymes or enzyme mixtures are commercially available, such as Flavourzyme® 1000 L from Novozymes, which is a peptidase preparation from *Aspergillus oryzae*, the Acylase Amano from Amano Enzyme Inc and the Acylase from *Penicillium* sp. from Fluka.

In a preferred embodiment the enzyme mixture Flavourzyme® 1000 L from Novozymes or an enzyme preparation containing the hydrolase of SEQ ID NO 1 as defined above can be used.

In another preferred embodiment the hydrolase of SEQ ID NO 1 can be obtained by expressing the enzyme in a suitable host such as e.g. of *Pichia pastoris* and secreted into the fermentation media.

The hydrolase of SEQ ID NO 1 preferably is a leucine amide peptidase 2 (LAP2).

Alternatively, hydrolases can be selected which can form the (R)-piperazine-2-carboxylic acid of the formula Ib Ib

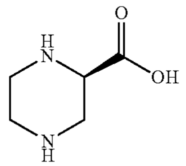

Commercially available enzymes that form the (R)-enantiomer can be e.g. ADDZYME *Bacillus subtilis* protease from Advanced Enzyme Technologies.

The enzymatic conversion is performed at a reaction temperature of 10° C. to 50° C., preferably of 20° C. to 30° C. in the solvent used in the previous hydrogenation step, preferably in water.

The substrate loading is as a rule kept below 30% w/v preferably between 1% w/v and 25% w/v.

Typically, the reaction does not require an extra buffer as the amino acid are buffering the reaction pH between 7.3 and 8.3.

Some enzymes, like the hydrolase of SEQ ID NO 1, may require the addition of a metal cofactor such as zinc, which is added in the form of a suitable salt.

Once the enzymatic conversion is completed piperazine-2-carboxylic acid of formula I can be isolated following procedures known to the skilled in the art.

However, in a preferred embodiment the reaction mixture with the chiral piperazine-2-carboxylic acid of formula I is converted into its hydrochloride salt by adding aqueous hydrochloric acid having a HCl concentration of 10% to 37% to the reaction mixture in a manner that the reaction mixture temperature is maintained in the range of 10° C. to 30° C., preferably 15° C. to 25° C.

It is further preferred to concentrate the reaction mixture under a reduced pressure of 30 mbar to 120 mbar at temperatures of 30° C. to 50° C. prior to the addition of the hydrochloric acid.

Under these conditions the chiral piperazine-2-carboxylic acid of formula I, preferably the piperazine-2-carboxylic acid of formula Ia, usually precipitates as hydrochloride salt and can, after filtration and washing of the filter cake with an aqueous hydrochloric acid and after drying, be obtained in crystalline form.

Step c)

Step c) is optional and requires the introduction of an amino protecting group PG to form the chiral piperazine-2-carboxylic acid derivative of formula IV

IV

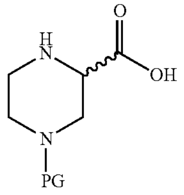

wherein PG stands for an amino protecting group.

Suitable amino protecting groups are as defined above, most preferred amino protecting group PG is Boc (tert-butoxycarbonyl).

For the introduction of the Boc group a typical bocylation agent such as di-tert-butyl dicarbonate ($Boc_2O$) or 2-(tert-butoxycarbonyloxyimino)-2-phenylacetonitrile (Boc ON), but preferably $Boc_2O$ can be used.

The reaction is usually performed in the presence of a base selected from an alkali carbonate such as potassium carbonate, sodium carbonate or calcium carbonate, an alkali hydrogen carbonate, such as sodium hydrogen carbonate, an alkali hydroxide, such as sodium hydroxide or a tertiary amine such as triethylamine. Preferably, an alkali carbonate, more preferably potassium carbonate is used. Suitable solvents are water, methanol, ethanol, acetone, acetonitrile, dioxane or mixtures thereof. In a preferred embodiment, a mixture of water and acetone is used.

The reaction temperature is as a rule selected between −15° C. and 30° C., preferably between 15° C. and 30° C.

In a preferred embodiment the (2S)-4-tert-butoxycarbonylpiperazine-2-carboxylic acid of formula IVa IVa

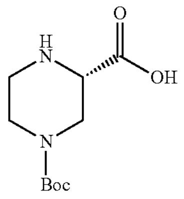

is formed.

In a further embodiment of the invention the process of the present invention can be applied in a process for the preparation of compounds of the formula X

X

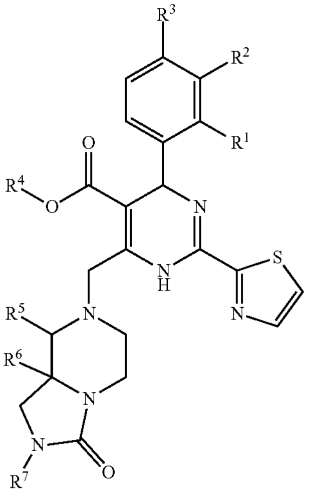

wherein $R^1$ is halogen or $C_{1-6}$-alkyl;

$R^2$ is hydrogen or halogen;

$R^3$ is hydrogen or halogen;

$R^4$ is $C_{1-6}$-alkyl;

$R^5$ is hydrogen or carboxy;

$R^6$ is hydrogen;

$R^7$ is $C_{1-6}$-alkyl, $C_{3-7}$-cycloalkyl, $-C_mH_{2m}-COOH$, $-C_mH_{2m}-C_{3-7}$-cycloalkyl-COOH or carboxyphenyl;

m is 1-6;

or pharmaceutically acceptable salts, or enantiomers or diastereomers thereof. The 5 compounds of formula X, together with meanings and definitions of m and $R^1$ to $R^7$ and processes thereto are disclosed in the PCT Publication WO 2015/132276, which is herein incorporated by reference. The formula X corresponds with formula IAA in WO 2015/132276 (page 22).

More preferred are the compounds of formula XX

XX

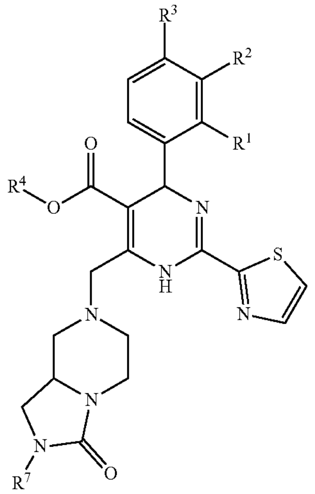

wherein $R^1$ to $R^4$ and $R^7$ are as above.

An essential intermediate in the process for the preparation of the compound of formula XX is the intermediate IX or enantiomers or diastereomers thereof.

IX

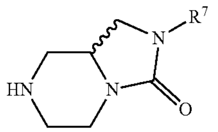

wherein $R^7$ is as outlined above.

The preparation of the compound of formula X further comprise the steps d) the conversion of the chiral piperazine-2-carboxylic acid of formula IV, or of a salt thereof,

IV

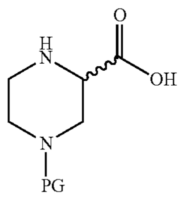

wherein PG is an amino protecting group, with an amine $R^7$—$NH_2$, wherein $R^7$ is as above, in the presence of a coupling agent and a base to form the mixed urea of formula V or of a salt thereof,

V

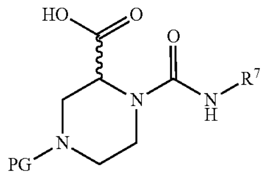

wherein PG and $R^7$ are as above;

e) the cyclisation of the mixed urea of formula V to form the hydantoin of formula VI

VI

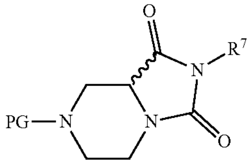

wherein PG and $R^7$ are as above;

f) the reduction of the hydantoin of formula VI to form the cyclic urea of formula VII

VII

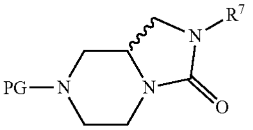

wherein PG and $R^7$ are as above; and g) the deprotection and formation of the compound of formula IX.

In a preferred embodiment, the intermediate IX can be of formula IXa or IXb

IXa

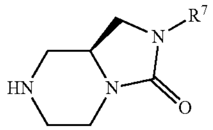

IXb

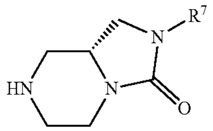

wherein $R^7$ is as defined above.

In a more preferred embodiment, the intermediate IX is of formula IXa.

The salts of the chiral piperazine-2-carboxylic acid derivative of formula IVb can be prepared by methods known to the skilled in the art.

The sodium salt can for instance be prepared by reacting the chiral piperazine-2-carboxylic acid derivative of formula IV with a methanolic aqueous sodium hydroxide solution in analogy to example of 4.3.6 of M. Laars et al, Tetrahedron: Asymmetry 21 (2010) 562-565.

Scheme 1 further illustrates the formation of the intermediate IX.

GC=gas chromatography
ID=internal diameter

Scheme 1

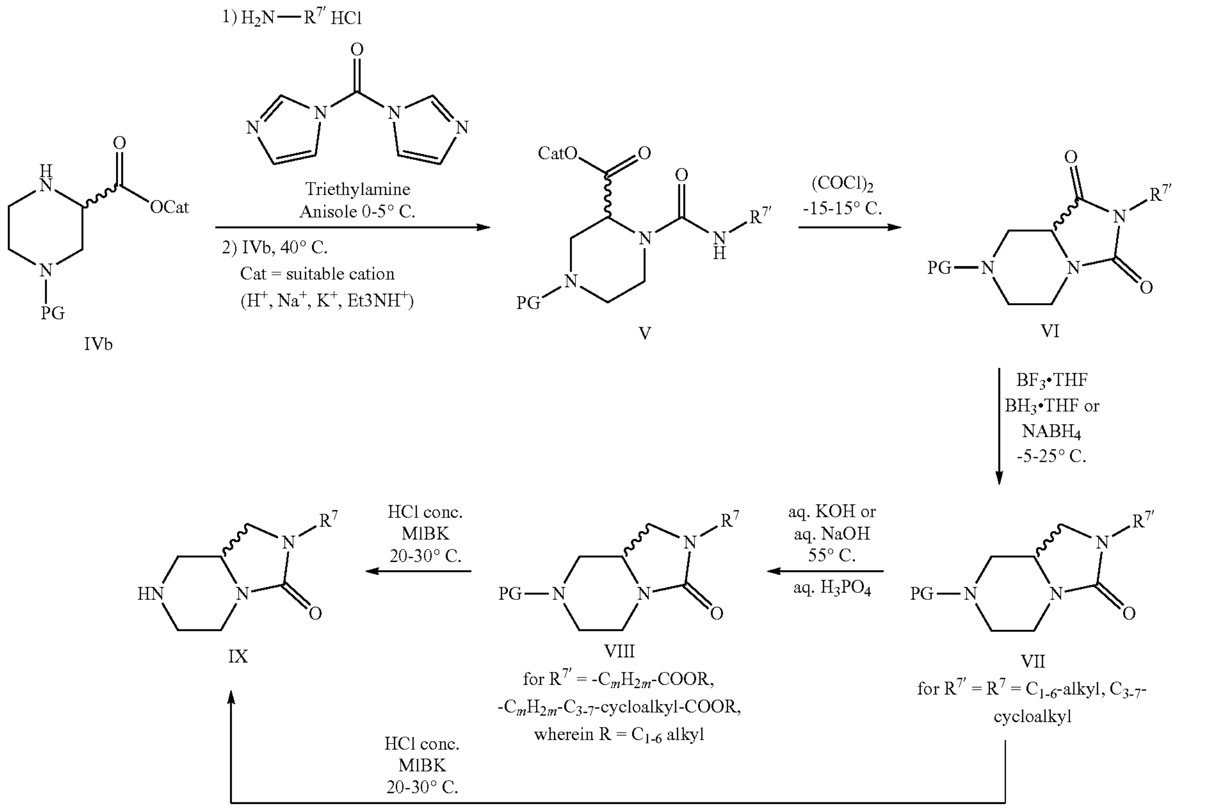

The mixed urea (V) can be prepared from the amine RT-$NH_2$ salt by coupling it with a chiral piperazine-2-carboxylic acid, or with a salt thereof (IVb) in the presence of a coupling agent such as carbonyldiimidazole (CDI) and a suitable base such as triethylamine. Suitable chiral piperazine-2-carboxylic acid salts (IVb) are alkali metal salts like the sodium- or the potassium-salt, or an ammonium salt like the triethylammonium salt. Cyclisation of the mixed urea (V) suitably with oxalyl chloride provides the hydantoin (VI). The subsequent reduction with a reducing agent selected from $BH_3$·THF or $NaBH_4$, in presence of $BF_3$·THF can afford the cyclic urea (VII). In case RT is an ester group saponification with an aqueous sodium or potassium hydroxide gives the corresponding acid (VIII). Boc-deprotection of compounds (VII) or (VIII) can be achieved with concentrated HCl in MIBK to form compound (IX). Compound (IXa) or (LXb) with absolute configuration can be obtained according to the synthesis of Scheme 1 with corresponding chiral starting material compound (IVb).

EXAMPLES

Abbreviations a %=area %
AOX I=alcohol oxidase I
BMMY=buffered methanol-complex medium (with) yeast extract
df=film thickness
L=length
MeOH=methanol
MIBK=methyl isobutylketone
OD=optical density
RCF=relative centrifugal force
RRT=relative retention time
XRF=X-ray fluorescence
YPD=yeast extract peptone dextrose

Example 1

(S)-Piperazine-2-carboxylic acid a) Preparation of rac-piperazine-2-carboxamide

Pyrazine-2-carboxamide (100 g, 812 mmol) was suspended in 300 mL of water in a pressure vessel that was then inertized with argon. 10% Pd/C (dry, 10.0 g) was added to the reaction mixture together with additional 30 mL of water, to rinse the reactor walls. The reactor was sealed, the atmosphere exchanged to hydrogen and the reaction mixture heated to 40° C. The atmosphere adjusted to 20 bar $H_2$ and the mixture stirred at 40° C. for 18 h, while maintaining a constant hydrogen pressure of 20 bar inside the vessel and recording the gas consumption over time. The reactor was cooled to room temperature, the atmosphere exchanged for argon and the reaction progress checked by GC analysis (conversion >99 a %, 97 a % title compound). The mixture was filtered with additional 170 mL of water to afford an aqueous solution, whose pH was then adjusted to 7.8 by slow addition of concentrated (37%) aqueous HCl (55 mL, 655 mmol), while keeping its temperature lower than 25° C. The resulting solution was directly subjected to the following step without isolation of the product.

GC Method description: Stationary phase: Agilent HP-5 (L=30 m. ID=0.32 mm, df=0.25 μm, max. temp. 350° C.): Temperature program: starting at 100° C. heating rate of 10° C./min up to 350° C. hold time at 350° C. 2 min, then cooling rate of 40° C./min to 100° C. hold time at 100° C. 0.75 min: Run time 34.0 min: Inlet mode: Constant pressure; Inlet initial pressure: 5.0 psi: Inlet initial flow 0.727 mL/min at 100° C. (starting oven temperature): Initial velocity 16.05 cm/s at 100° C. (starting oven temperature): Split ratio, split flow 1:30, 41.38 mL/min: Injection volume 1.0 μL: Inlet temperature 280° C.: Detector temperature 320° C.: Detector $H_2$ flow (fuel flow) 40 mL/min: Detector Air flow (oxidizer flow) 400 mL/min: Detector $N_2$ flow (const. makeUp) 30 mL/min; Retention times: pyrazine-2-carboxamide=4.56 min ($RRT_{approx}$=0.71), rac-piperazine-2-carbocxamide=6.46 min (RRT=1.0).

b) Preparation of rac-piperazine-2-carboxamide (Catalyst Reuse)

Pyrazine-2-carboxamide (10 g. 81.2 mmol) was suspended in 50 ml of water in a pressure vessel equipped with a deep-tube having a 2 μm frit. The vessel was then inertized with argon. 10% Pd/C (dry. 1.0 g) was added to the reaction mixture and the reactor was sealed, the atmosphere exchanged to hydrogen and the reaction mixture heated to 40° C. The atmosphere was adjusted to 20 bar $H_2$ and the mixture stirred at 40° C. for 18 h. while maintaining a constant hydrogen pressure of 20 bar inside the vessel and recording the gas consumption over time. The reactor was cooled to room temperature, the atmosphere exchanged for argon and the reaction mixture was filtered out of the reactor through the deep-tube using an over-pressure of Ar. The resulting solution was analyzed by GC and by XRF spectroscopy to determine the presence of traces of Pd. The vessel was depressurized and charged again with 10 g pyrazine-2-carboxamide and water (50 mL) to repeat the hydrogenation re-using the filtered catalyst. This procedure was repeated for 5 times, always achieving >98 a % conversion and >92 a % yield (as judged by GC analysis) and levels of Pd in solutions always <2 ppm (as judged by XRF spectroscopy analysis).

c) Preparation of(S)-piperazine-2-carboxylic acid dihydrochloride salt

To the pH-adjusted solution of rac-piperazine-2-carboxamide solution of example 1a (105 g: 812 mmol dissolved in approx. 555 mL water at pH 7.8), the enzyme catalyst was added (Flavourzyme® 1000 L (Novozyme). 50 mL) and reaction was stirred for 22 h at room temperature. Reaction was monitored by HPLC and showed 47 a % acid formation after 20 h. The resulting reaction mixture was concentrated to approx. 400 mL under reduced pressure (30)-120 mbar. 45° C.) and subsequently concentrated (37%) aqueous HCl was added to the reaction mixture (190) mL, 2.28 mol) over 45 min to precipitate the (S)-piperazine-2-carboxylic acid dihydrochloride salt and stirred for 4 h in order to ensure complete product precipitation. 35 Resulting crystals were filtered off and washed with HCl (3 N, 120 mL, 360 mmol) and dried under reduced pressure (5 mbar, 45° C., 24 h) to give the desired product in 38% yield (62 g) with 87 a % purity and >99% ee.

LC chiral method description (for ee-determination)-Stationary phase: Astec Chirobiotic T (L=25 cm, ID=4.6 mm, particle size=5 μm).

Eluents: A) Potassium phosphate 50 mM pH 7.0 B) methanol; Pump program: isocratic 90 A: 10 B, run time 13 min, flow: 1.0 mL/min: Column oven temperature: 10° C.: Injection volume: 2 μL: Detection: DAD 198 nm.

Retention times: (S)-piperazine-2-carboxylic acid=4.42 min, (R)-piperazine-2-carboxylic acid=4.82 min, rac-piperazine-2-carboxamide=10.43 min.

NMR data of(S)-piperazine-2-carboxylic acid dihydrochloride salt.

$^1$H NMR (600 MHZ, $D_2O$) δ ppm: 4.17 (dd, J=11.3, 3.9 Hz, 1H), 3.91 (dd, J=14.1, 3.8 Hz, 1H), 3.73 (dt, J=14.0, 3.3 Hz, 1H), 3.69-3.63 (m, 1H), 3.48-3.41 (m, 2H), 3.39-3.33 (m, 1H).

d) Preparation of(S)-piperazine-2-carboxylic acid using a Prep. Of Seq. ID 1 d1) Enzyme Preparation of SEQ ID NO 1

The enzyme DNA sequence was integrated into a *Pichia pastoris* expression/integration plasmid, and after linearization the sequence was integrated stably into the genome of an Mut+ wild type *Pichia pastoris* strain into the AOX I locus by homologous recombination. Recombinant strains with integrated expression cassette were selected using a Zeocin antibiotic resistance marker. The target protein expression is under the control of the endogenous inducible AOX I promotor, and the expressed protein was secreted into the culture supernatant via a cleavable N-terminal fusion with the *S. cerevisiae* alpha mating factor secretion signal peptide.

Overnight cultures of a single colony of the recombinant strains were grown in YPD medium without antibiotic selection (Sigma Aldrich Y1375, ready-made medium powder).

To produce the enzyme, an expression culture in BMMY medium (110 mL) was inoculated with the corresponding YPD overnight culture to a final OD600 of 1 using 500 mL shake flasks. The target protein expression in the culture was induced by activating the AOX promotor by addition of 1% MeOH (v/v). Supplementary 1.5% (v/v) methanol was added over the course of the 3 days of expression twice per 24 h (6×1.5 mL 100% MeOH in total during 3 days), while the culture was shaken at 180 rpm at 28° C.

After 3 days, the expression culture supernatant was clarified by centrifugation (RCF 12000×g, 15 min), frozen at −80° C., and subsequently lyophilized (−80° C./100 μbar) without performing any further processing steps.

The lyophilized powders derived were used without any further purification steps.

d2) Preparation of(S)-piperazine-2-carboxylic acid rac-Piperazine-2-carboxamide (2 g, 15 mmol) was dissolved in 2 N HCl (6 mL, 12 mmol) and water was added (2 mL) to result in a solution 20% (w/v) solution of rac-2-piperazinecarboxamide with pH 7.8.

To an aliquot of this solution (1 mL) enzyme preparation containing SEQ ID NO 1. was added (100 mg, lyophilized powder) and a $ZnCl_2$ solution (1 M, 20 μL).

Reaction was incubated for 2 days at room temperature under shaking in an Eppendorf ThermoMixer C.

The reaction mixture formed the desired product(S)-piperazine-2-carboxylic acid with 22 a % and >98% ee.

Example 2

(S)-piperazine carboxylic acid dihydrochloride salt a) Preparation of(S)-piperazine carboxylic acid dihydrochloride salt (Flavourzyme)

To the pH-adjusted solution of rac-2-piperazinecarboxamide solution of example 1a (105 g: 812 mmol dissolved in approx. 555 mL water at pH 7.8) the enzyme catalyst was added (100 g, Flavourzyme® 1000 L (Novozymes)) and reaction was stirred for 21 h at room temperature. The reaction was monitored by HPLC and showed 52% acid formation.

The resulting reaction mixture was concentrated to approx. 530 g under reduced pressure (30-120 mbar, 45° C.) and subsequently cooled to 20-23° C. (ice cooling) prior to the addition of concentrated (37%) aqueous HCl (190 mL, 2.28 mol, 2.8 eq.) over 30 min to precipitate the (S)-piperazine carboxylic acid dihydrochloride salt. Further stirring for 4.5 h ensures complete product precipitation at room temperature.

Resulting crystals were filtered off and washed with HCl (3 N, 120 mL, 360 mmol) and dried at high vacuum over night to give the desired product in 40% yield (69 g) with 97 a % purity and 99.1% ee.

b1) Enzyme Preparation of Leucine Amide Peptidase 2 (LAP2)

Enzymes were produced in analogy to Example 1, d1) with the variation that expression was conducted in a fermenter on 10 L scale as known by the person skilled in the art. 2 parallel cultivated 10 L LAP2 fed-batch *Pichia pastoris* bioreactors were grown in fed-batch mode using glycerol as carbon source for 26 h. After depletion of the glycerol feed, the recombinant LAP2 protein expression was induced by pulsed addition of 3% of the culture volume of 100% methanol, this was repeated ~26 times after depletion of the previous pulse, for a total of 96 h runtime. Supernatants were combined and filtrated using a 0.2 μM PES Repligen hollow fibre membrane (12 L/min feed flow. 0.07 MPa transmembrane pressure): the remaining 1.2 L retentate was washed with 4× 500 mL dH2O and then discarded. The resulting filtrate was concentrated to ~2 L using a 10 kDa mPES Repligen hollow fibre membrane (12 L/min feed flow. 0.12 MPa transmembrane pressure). The concentrate was submitted to buffer exchange at constant volume at 12 L/min feed flow and 0.12 MPa transmembrane pressure using 10 L of 25 mM sodium acetate buffer. 100 mM NaCl. 0.5 mM $ZnCl_2$, pH 5.6 buffer. The resulting solution was then concentrated to ~1.25 L and filter-sterilized using a 0.2 μm mPES bottle top filter.

b2) Preparation of(S)-piperazine carboxylic acid dihydrochloride salt (LAP 2)

To the pH-adjusted solution of rac-2-piperazinecarboxamide solution of example 1a (105 g: 812 mmol dissolved in approx. 555 mL water at pH 7.8). The enzyme catalyst was added (25 ml of leucine amide peptidase 2 (LAP 2) formulation: SEQ ID NO 1) and reaction was stirred for 19 h at room temperature. The reaction was monitored by HPLC and showed 53% acid formation. The resulting reaction mixture was concentrated to approx. 500 g under reduced pressure (30-120 mbar. 45° C.) and subsequently cooled to 20-23° C. (ice cooling) prior to the addition of concentrated (37%) aqueous HCl (190 mL, 2.28 mol. 2.8 eq) over 30 min to precipitate the (S)-piperazine carboxylic acid dihydrochloride salt. Further stirring for 4.5 h ensures complete product precipitation at room temperature.

Resulting crystals were filtered off and washed with HCl (3 N, 120 mL, 360 mmol) and dried at high vacuum over night to give the desired product in 41% yield (69 g) with 98 a % purity and >99% ee.

Example 3 a) Preparation of (2S)-4-tert-butoxycarbonylpiperazine-2-carboxylic acid (S)-Piperazine-2-carboxylic acid dihydrochloride salt (10.8 g: 50 mmol) and potassium carbonate (7.3 g: 53 mmol) were combined in aqueous acetone (17 g acetone and 85 g water). The solution obtained was filtered over celite (1 g) to remove any remaining enzyme residue from the preceding step. A solution of Boc-anhydride (12 g) in acetone (17 g) was dosed over 4 h to the solution during which the product gradually crystallized. After the end of the dosage the pH of the reaction mixture was adjusted from pH 6 back to pH 7 with potassium bicarbonate (0.42 g) in water (2 g). Stirring was continued overnight to ensure complete product precipitation. The residue was filtered, washed with aqueous acetone (11 g acetone and 1 g water) and acetone (12 g), and the wet cake was dried at 45° C./12 mbar overnight to afford 8.8 g of title compound.

NMR and MS data of (2S)-4-tert-butoxycarbonylpiperazine-2-carboxylic acid.

$^1$H NMR (600 MHZ, $D_2O$) δ ppm: 4.30 (ddd, J=14.6, 4.1, 1.0 Hz, 1H), 4.04 (br s, 1H), 3.78 (dd, J=10.0, 4.0 Hz, 1H), 3.45 (br d, J=12.8 Hz, 1H), 3.33 (ddd, J=14.5, 10.9, 3.3 Hz, 1H), 3.39 (br s, 1H), 3.15 (ddd, J=12.9, 10.7, 3.8 Hz, 1H), 1.48 (s, 9H)

MS $[M-H]^-$ at m/z=229.1.

b) Preparation of (2S)-4-tert-butoxycarbonylpiperazine-2-carboxylic acid

To a mixture of(S)-Piperazine carboxylic acid dihydrochloride salt (50 g: 246 mmol), acetone (77.9 g) and water (347 g) a solution of potassium carbonate (34 g: 246 mmol) in water (47.2 g) was slowly added. The solution obtained was stirred with celite (5 g) for 10 min, and filtered to remove any remaining enzyme residue from the preceeding step. The filter residue was washed with aqueous acetone (13 g acetone and 34 g water). At 20° C., a solution of Boc-anhydride (56.4 g, 259 mmol) in acetone (77.9 g) was dosed over 4 h to the solution during which the product gradually crystallized. After the end of the dosage the pH of the reaction mixture was adjusted from pH 5.5 to pH 7 with 15 ml of a prepared solution consisting of potassium bicarbonate (12.3 g) and water (50 g). Stirring was continued overnight to ensure complete product precipitation. The residue was filtered, washed with aqueous acetone (44 g acetone and 4 g water) and acetone (40 g), and the wet cake was dried at 43° C./5 mbar/6 h to afford 38.25 g of title compound.

$^1$H NMR (600 MHZ, $D_2O$) δ ppm: 4.30 (ddd, J=14.6, 4.1, 1.0 Hz, 1H), 4.04 (br s, 1H), 3.78 (dd, J=10.0, 4.0 Hz, 1H), 3.45 (br d, J=12.8 Hz, 1H), 3.33 (ddd, J=14.5, 10.9, 3.3 Hz, 1H), 3.39 (br s, 1H), 3.15 (ddd, J=12.9, 10.7, 3.8 Hz, 1H), 1.48 (s, 9H)

MS $[M-H]^-$ at m/z=229.1.

The invention claimed is:

1. A process for preparing a compound of formula IX:

IX

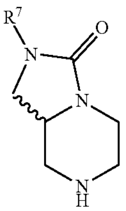

or a stereoisomer thereof, wherein:

$R^7$ is $C_{1-6}$ alkyl, $C_mH_{2m}$—C(O)OR, $C_mH_{2m}$—$C_{3-7}$ cycloalkyl-C(O)OR, $C_{3-7}$ cycloalkyl, or phenyl-C(O)OR;

R is H or $C_{1-6}$ alkyl;

m is 1, 2, 3, 4, 5, or 6; and

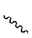 is 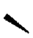 or 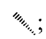;

wherein the process comprises the following steps:

(a) reacting a compound of formula II:

II

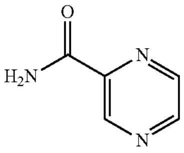

with hydrogen in the presence of a solvent and a palladium catalyst or a platinum catalyst, to form a compound of formula III:

III

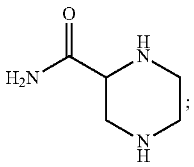

;

(b) reacting the compound of formula III formed in step (a) above with a hydrolase selected from the group consisting of an amidase and a peptidase, or a mixture thereof, to form a compound of formula I:

I

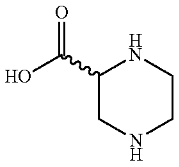

or a salt or stereoisomer thereof, wherein:

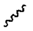 is 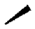 or 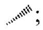;

(c) protecting the compound of formula I formed in step (b) above, or a salt or stereoisomer thereof, with an amino protecting group (PG) selected from the group consisting of di-tert-butyl dicarbonate ($Boc_2O$) and 2-(tert-butoxycarbonyloxyimino)-2-phenylacetonitrile, to form a compound of formula IV:

IV

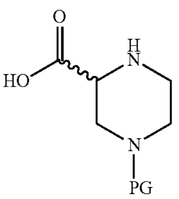

or a salt or stereoisomer thereof, wherein:

is or ;

(d) reacting the compound of formula IV formed in step (c) above, or a salt or stereoisomer thereof, with a compound of the following formula:

$R^7$—$NH_2$, wherein:

$R^7$ is $C_{1-6}$ alkyl, $C_mH_{2m}$—C(O)OR, $C_mH_{2m}$—$C_{3-7}$ cycloalkyl-C(O)OR, $C_{3-7}$ cycloalkyl, or phenyl-C(O)OR;

R is H or $C_{1-6}$ alkyl; and m is 1, 2, 3, 4, 5, or 6;

in the presence of a base and the coupling agent, carbonyldiimidazole (CDI), to form a compound of formula V:

V

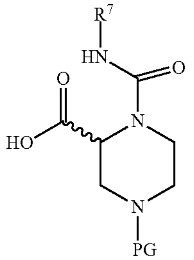

or a salt or stereoisomer thereof, wherein:

PG is $C(O)OC(CH_3)_2$;

$R^7$ is $C_{1-6}$ alkyl, $C_mH_{2m}$—C(O)OR, $C_mH_{2m}$—$C_{3-7}$ cycloalkyl-C(O)OR, $C_{3-7}$ cycloalkyl, or phenyl-C(O)OR;

R is H or $C_{1-6}$ alkyl;

m is 1, 2, 3, 4, 5, or 6; and is or ;

(e) reacting the compound of formula V formed in step (d) above, or a salt or stereoisomer thereof, with oxalyl chloride, to form a compound of formula VI:

VI

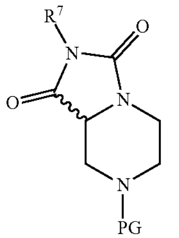

or a stereoisomer thereof, wherein:

PG is $C(O)OC(CH_3)_2$;

$R^7$ is $C_{1-6}$ alkyl, $CH_{2m}$—C(O)OR, $C_mH_{2m}$—$C_{3-7}$ cycloalkyl-C(O)OR, $C_{3-7}$ cycloalkyl, or phenyl-C(O)OR;

R is H or $C_{1-6}$ alkyl;

m is 1, 2, 3, 4, 5, or 6; and is or ;

(f) reacting the compound of formula VI formed in step (e) above, or a stereoisomer thereof, with a reducing agent selected from the group consisting of $BH_3$·THF and $NaBH_4$, to form a compound of formula VII:

VII

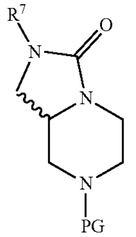

or a stereoisomer thereof, wherein:

PG is $C(O)OC(CH_3)_2$;

$R^7$ is $C_{1-6}$ alkyl, $C_mH_{2m}$—C(O)OR, $C_mH_{2m}$—$C_{3-7}$ cycloalkyl-C(O)OR, $C_{3-7}$ cycloalkyl, or phenyl-C(O)OR;

R is H or $C_{1-6}$ alkyl;

m is 1, 2, 3, 4, 5, or 6; and is or ; and (g) deprotecting the compound of formula VII formed in step (f) above, or a stereoisomer thereof, with concentrated HCl in methyl isobutyl ketone (MIBK), to form a compound of formula IX:

IX

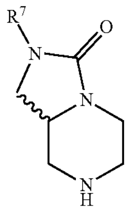

or a stereoisomer thereof, wherein:

$R^7$ is $C_{1-6}$ alkyl, $C_mH_{2m}$—C(O)OH, $C_mH_{2m}$—$C_{3-7}$ cycloalkyl-C(O)OH, $C_{3-7}$ cycloalkyl, or phenyl-C(O)OH;

m is 1, 2, 3, 4, 5, or 6; and is or .

2. The process of claim 1, wherein in step (a), the solvent is an organic solvent selected from the group consisting of an aliphatic alcohol and water, or a mixture thereof.

3. The process of claim 1, wherein:

(i) in step (a), the palladium catalyst or platinum catalyst has an inert support selected from the group consisting of aluminum oxide and carbon; and (ii) in step (a), the palladium catalyst or platinum catalyst has a metal loading on the inert support in the range of from 0.5% w/w to 20% w/w.

4. The process of claim 1, wherein in step (a), the palladium catalyst or platinum catalyst is recycled.

5. The process of claim 1, wherein:

(i) in step (a), the reaction is performed at a temperature in the range of from 20° C., to the boiling temperature of the solvent; and (ii) in step (a), the reaction is performed at a hydrogen pressure in the range of from 5 bar to 50 bar.

6. The process of claim 1, wherein:

(i) in step (a), the compound of formula III is not isolated; and (ii) in step (a), the compound of formula III is further processed in situ in step (b).

7. The process of claim 1, wherein:

(i) in step (b), the reaction is performed at a temperature in the range of from 10° C., to 50° C.; and (ii) in step (b), the reaction is performed in the same solvent used in step (a).

* * * * *

SEQUENCE LISTING

<160> NUMBER OF SEQ ID NOS: 1

<210> SEQ ID NO 1
<211> LENGTH: 496
<212> TYPE: PRT
<213> ORGANISM: Aspergillus oryzae

<400> SEQUENCE: 1

Met Arg Ser Leu Leu Trp Ala Ser Leu Leu Ser Gly Val Leu Ala Gly
1 5 10 15

Arg Ala Leu Val Ser Pro Asp Glu Phe Pro Glu Asp Ile Gln Leu Glu
20 25 30

Asp Leu Leu Glu Gly Ser Gln Gln Leu Glu Asp Phe Ala Tyr Ala Tyr
35 40 45

Pro Glu Arg Asn Arg Val Phe Gly Gly Lys Ala His Asp Asp Thr Val
50 55 60

Asn Tyr Leu Tyr Glu Glu Leu Lys Lys Thr Gly Tyr Tyr Asp Val Tyr
65 70 75 80

Lys Gln Pro Gln Val His Leu Trp Ser Asn Ala Asp Gln Thr Leu Lys
85 90 95

Val Gly Asp Glu Glu Ile Glu Ala Lys Thr Met Thr Tyr Ser Pro Ser
100 105 110

Val Glu Val Thr Ala Asp Val Ala Val Val Lys Asn Leu Gly Cys Ser
115 120 125

Glu Ala Asp Tyr Pro Ser Asp Val Glu Gly Lys Val Ala Leu Ile Lys
130 135 140

Arg Gly Glu Cys Pro Phe Gly Asp Lys Ser Val Leu Ala Ala Lys Ala
145 150 155 160

Lys Ala Ala Ala Ser Ile Val Tyr Asn Asn Val Ala Gly Ser Met Ala
165 170 175

Gly Thr Leu Gly Ala Ala Gln Ser Asp Lys Gly Pro Tyr Ser Ala Ile
180 185 190

Val Gly Ile Ser Leu Glu Asp Gly Gln Lys Leu Ile Lys Leu Ala Glu
195 200 205

Ala Gly Ser Val Ser Val Asp Leu Trp Val Asp Ser Lys Gln Glu Asn
210 215 220

Arg Thr Thr Tyr Asn Val Val Ala Gln Thr Lys Gly Gly Asp Pro Asn
225 230 235 240

Asn Val Val Ala Leu Gly Gly His Thr Asp Ser Val Glu Ala Gly Pro
245 250 255

Gly Ile Asn Asp Asp Gly Ser Gly Ile Ile Ser Asn Leu Val Ile Ala
260 265 270

Lys Ala Leu Thr Gln Tyr Ser Val Lys Asn Ala Val Arg Phe Leu Phe
275 280 285

Trp Thr Ala Glu Glu Phe Gly Leu Leu Gly Ser Asn Tyr Tyr Val Ser
290 295 300

His Leu Asn Ala Thr Glu Leu Asn Lys Ile Arg Leu Tyr Leu Asn Phe
305 310 315 320

Asp Met Ile Ala Ser Pro Asn Tyr Ala Leu Met Ile Tyr Asp Gly Asp
325 330 335

Gly Ser Ala Phe Asn Gln Ser Gly Pro Ala Gly Ser Ala Gln Ile Glu
340 345 350

Lys Leu Phe Glu Asp Tyr Tyr Asp Ser Ile Asp Leu Pro His Ile Pro
355 360 365

-continued

```
Thr Gln Phe Asp Gly Arg Ser Asp Tyr Glu Ala Phe Ile Leu Asn Gly
    370                 375                 380

Ile Pro Ser Gly Gly Leu Phe Thr Gly Ala Glu Gly Ile Met Ser Glu
385                 390                 395                 400

Glu Asn Ala Ser Arg Trp Gly Gly Gln Ala Gly Val Ala Tyr Asp Ala
                405                 410                 415

Asn Tyr His Ala Ala Gly Asp Asn Met Thr Asn Leu Asn His Glu Ala
            420                 425                 430

Phe Leu Ile Asn Ser Lys Ala Thr Ala Phe Ala Val Ala Thr Tyr Ala
        435                 440                 445

Asn Asp Leu Ser Ser Ile Pro Lys Arg Asn Thr Thr Ser Ser Leu His
    450                 455                 460

Arg Arg Ala Arg Thr Met Arg Pro Phe Gly Lys Arg Ala Pro Lys Thr
465                 470                 475                 480

His Ala His Val Ser Gly Ser Gly Cys Trp His Ser Gln Val Glu Ala
                485                 490                 495
```